United States Patent [19]

Tafesh et al.

[11] Patent Number: 5,220,066
[45] Date of Patent: Jun. 15, 1993

[54] PROCESS FOR THE PREPARATION OF ARYLETHYLAMINES AND SUBSTITUTED ARYLETHYLAMINES

[75] Inventors: Ahmed Tafesh; B. Frank Wood; Joseph A. McDonough; Graham N. Mott, all of Corpus Christi, Tex.

[73] Assignee: Hoechst Celanese Corporation, Somerville, N.J.

[21] Appl. No.: 859,773

[22] Filed: Mar. 30, 1992

[51] Int. Cl.[5] ............................................. C07C 209/40
[52] U.S. Cl. ........................................ 564/375; 562/59; 562/66; 562/125; 564/323; 564/337; 564/374; 564/378; 564/382
[58] Field of Search ............... 564/323, 337, 375, 374, 564/378, 381, 382; 562/59, 66, 125

[56] References Cited

U.S. PATENT DOCUMENTS 5,041,669  8/1991  Tafesh et al. .................. 564/337

Primary Examiner—Richard L. Raymond
Attorney, Agent, or Firm—Donald R. Cassady; James J. Mullen; P. S. Kalanaraman

[57] ABSTRACT

This invention provides a process for directly preparing arylethylamines and their salts from (α-halo-α-oximino)acetophenones. The process involves hydrogenation in presence of a transition metal catalyst. The process is illustrated by conversion of 4-hydroxy-(α-chloro-α-oximino)acetophenone to Tyramine hydrochloride:

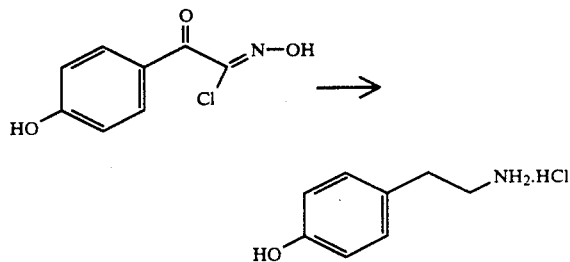

24 Claims, No Drawings

PROCESS FOR THE PREPARATION OF ARYLETHYLAMINES AND SUBSTITUTED ARYLETHYLAMINES

This invention discloses a process for preparing arylethylamines and substituted arylethylamines by hydrogenation reduction of (α-chloro-α-oximino)acetophenones, and substituted (α-chloro-α-oximino)acetophenones.

BACKGROUND OF THE INVENTION

Substituted and unsubstituted arylethylamines and their salts are chemical intermediates of commercial significance. They are used in the preparation of pharmacologically active compounds and in some instances are themselves pharmacologically active. For example, phenethylamine and p-hydroxyphenethylamine (Tyramine) have sympathomimetic (adrenergic) action. Tyramine is also a moiety in opiates, and is useful as an intermediate or substituent in the preparation of other physiologically active compounds or compositions. Tyramine hydrochloride is an important pharmaceutical intermediate used for the preparation of bezafibrate, an anticholesterol agent. Hydroxytyramine (dopamine) is a pharmacologically important neural inhibitory transmitter. It is the active ingredient in Dopastat and Intropin, and it also represents the naturally occurring immediate precursor of norepinephrine.

Because of the importance of arylethylamines and their salts, accounts of their synthesis are well known. Some of them are: U.S. Pat. Nos. 1,995,709; 2,567,906; 2,505,645; 2,784,228; and 3,966,813; *Journal of Medicinal Chemistry*, vol. 25, p. 1442 (1982); *J. Chem. Society.* Vol. 95, p. 1127 (1909); *J. Amer. Chem. Society.* Vol. 55, p. 3389 (1933), and *Hakko Kogaku Kaishi*, Vol. 55(2), pp. 68–74 (1977).

U.S. Pat. No. 5,041,669 (assigned to Hoechst Celanese Corporation) describes the synthesis of arylethylamines from arylmethyl ketones. The ketones are converted to aryl α-oximinoalkyl ketones which are then hydrogenated to arylethylamines.

Pending U.S. patent application Ser. No. 07/630,127, filed Dec. 19, 1990, now abandoned, describes the synthesis of arylethylamine hydrochlorides by hydrogenation reduction of aryl α-oximinoalkyl ketones in an aqueous reaction medium.

There is a continuing interest in identifying improved and cost effective methods to prepare arylethylamines, preferably from readily available materials, or materials that may be produced readily and economically such as, for example, (α-chloro-α-oximino)acetophenones. Synthesis of (α-halo-α-oximino)acetophenones is known. For example, U.S. patent application Ser. No. 07/801,999, filed Dec. 3, 1991, describes the synthesis of 4-hydroxy (α-chloro-α-oximino)acetophenone (N,4-dihydroxy-α-oxobenzene-ethanimidoyl chloride). Compounds like 4-hydroxy (α-chloro-α-oximino)acetophenone are known to yield aryl aminoethanol hydrochlorides on reduction with lithium aluminum hydride, according to H. Brachwitz, *Zeitschrift fur Chemie.* Vol. 14(7), 268 (1974).

SUMMARY OF THE INVENTION

The present invention includes a method of selectively preparing arylethylamines and their salts from (α-chloro-α-oximino) acetophenones. The method comprises the steps of:

(a) providing a compound of the formula:

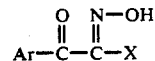

wherein X is a halide selected from F, Cl, Br, or I; and wherein Ar is an unsubstituted or substituted phenyl or naphthyl radical, wherein the substituents are selected from the group consisting of amino, alkylamino, dialkylamino, hydroxyl, alkoxy, alkyl, phenyl, benzyl, sulfonic acid, and sulfinic acid radicals, wherein the alkyl component is a branched or unbranched C1–C8 alkyl radical and wherein any of said alkyl, phenyl, and benzyl radicals are optionally substituted with one or more substituents selected from amino, hydroxyl, sulfonic acid, and sulfinic acid radicals, and said phenyl and benzyl substituents are optionally substituted with a C1–C8 alkyl or C1–C8 alkoxy radical or both;

(b) partially hydrogenating said compound of step (a) in a first hydrogenation step with hydrogen in the presence of a substantially anhydrous protic solvent and a transition metal catalyst under substantially anhydrous conditions to produce a first reaction mixture;

(c) adding water to said first reaction mixture; and (d) proceeding to further hydrogenate the reaction mixture of step (b) in a second hydrogenation step in the presence of water to produce arylethylamine salt, wherein at least one of said hydrogenation steps is carried out in the presence of an inorganic acid, and optionally, (e) basifying the salt to the free base arylethylamine.

As an illustration, when X is Cl, and Ar is 4-hydroxyphenyl, the starting compound is 4-hydroxy (α-chloro-α-oximino)acetophenone (Formula 2 infra), and the product is Tyramine hydrochloride.

The reaction steps (a) through (d) may be conducted in one pot, with no need for isolation of any intermediates. Since processes to convert amine salts to the free amines (step (e)) are well known, the instant invention provides a simple route to make arylethylamines.

DESCRIPTION OF THE INVENTION

The present invention provides, in a first embodiment, a process for selectively converting (α-halo-α-oximino)acetophenones to arylethylamines through the amine salts, as described in Scheme I:

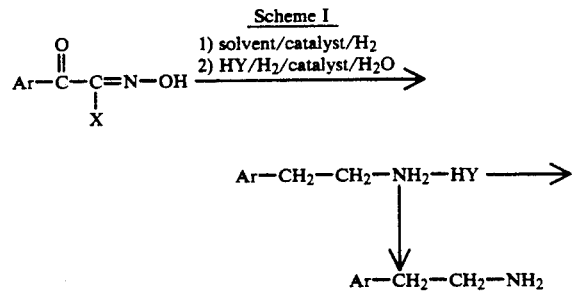

wherein X and Ar are as described above, and HY refers to an inorganic acid. The product formed thereby is the salt of the desired amine, which may be converted to the free amine by processes well known such as, for example, treating the salt with a base.

The reaction of Scheme I is a catalytic hydrogenation and is conducted in a solvent in which the compound of Formula 1 is preferably dissolved. Generally the concentration of the solution may be in the range of about 1-35 weight %, typically about 10-25%, and preferably about 18-25%. The solvent is a protic solvent such as, for example, alcohols, esters, ethers, acids, and the like, and the mixtures thereof. It is essential, however, that the solvent chosen is substantially anhydrous during step (b) (in SUMMARY above), and the hydrogenation conditions are substantially moisture-free. The presence of water loads to hydrolytic by-products derived from the starting material 1. The term "substantially anhydrous" refers to limitation of water content to less than 1% in the solvent. Such anhydrous solvents are commercially available. Substantially moisture-free conditions are achieved generally by maintaining an inert gas atmosphere, as is well known to those skilled in the art. Maintaining an inert gas atmosphere also helps in safe operation, since some of the reaction mixtures may tend to become flammable in presence of air or oxygen. Step (b) involves consumption of about 3 equivalents of hydrogen. The necessity to maintain anhydrousness does not exist after step (b); then aqueous inorganic acid HY is added and further hydrogenation for a consumption of 2 more equivalents of hydrogen is carried out.

The hydrogenation reaction is catalyzed by catalysts of the transition metal type on an inert support. Such catalysts are well known and available. Examples of transition metals include Pt, Pd, Raney Ni, Rh, and combinations thereof. Palladium and platinum are preferred with palladium being the most preferred. A preferred inert support is carbon. Such catalysts are commercially available as Pd/C, Pt/C, and the like. The catalyst is generally used in a concentration of about 0.05 to about 10 weight percent based on compound of Formula 1, typically in the range of about 0.05-7 weight percent and preferably in about 0.05-5 weight percent. The reaction during step (b) is generally conducted between about 10°-70° C., typically about 20°-60° C., and preferably about 40°-55° C. After addition of the aqueous inorganic acid, step (d) hydrogenation is carried out generally in the range of about 35°-120° C., typically about 30°-110° C., and preferably at about 50°-95° C.

The pressure range for hydrogen during the hydrogenation is generally about 0-1000 psi, typically about 0-500 psi, and preferably about 0-300 psi.

As noted above, the solvent for step (b) must be substantially anhydrous. This is because ($\alpha$-chloro-$\alpha$-oximino)acetophenones of Formula 1 may be prone to facile hydrolysis by water similar to acid halides, due to their structural similarity. Thus, if the solvent is not substantially anhydrous, any water in the solvent may lead to undesired products, in addition to or instead of, the desired arylethylamine salt, depending upon the amount of water in the reaction. For example, if 4-hydroxy ($\alpha$-chloro-$\alpha$-oximino)acetophenone is subjected to hydrogenation according to the invention but with employing an aqueous medium during step (b), substantial amounts of p-hydroxybenzoic acid are formed in the reaction. However, by employing a substantially anhydrous solvent as well as moisture-free conditions during step (b) of the reaction, the formation of p-hydroxybenzoic acid can be significantly reduced or avoided.

In another embodiment of the invention, instead of adding acid HY in step (c), it may be added, in its anhydrous form, to the solvent in step (b) itself, in such a way that the anhydrousness of the medium is not adversely affected. When such an addition is performed, then step (c) may consist of addition of water only. Thus, for example, if the solvent in step (b) is acetic acid, or methanol, an acid such as dry HCl may be added to that solvent in step (b). Then step (c) would consist of addition of water only.

In another embodiment of the invention, it is possible to entirely avoid adding both water and HY to the reaction. Thus, for example, if the hydrogenation is done in a solvent such as glacial acetic acid, good yields of the amine may be obtained, without adding HY and water in the hydrogenation. The consumption of all the needed hydrogen occurs in acetic acid.

In yet another embodiment, the process involves the conversion of 4-hydroxy ($\alpha$-chloro-$\alpha$-oximino)acetophenone (Formula 2) to Tyramine hydrochloride (Formula 3), as shown in Scheme II:

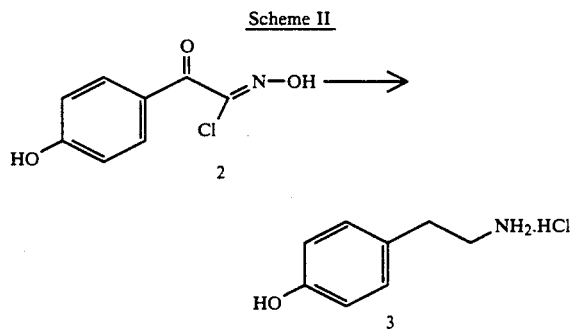

Thus, 4-hydroxy ($\alpha$-chloro-$\alpha$-oximino)acetophenone (2) is taken in a hydrogenation apparatus such as, for example, an autoclave, and a transition metal catalyst on an inert support such as, for example, 10% Pd/C is added to it. The atmosphere in the autoclave is made substantially moisture-free by providing an atmosphere of nitrogen, after which a substantially anhydrous solvent such as, for example, methanol is added in enough amounts to make about a 20 weight percent solution of compound 2 in methanol. The nitrogen is replaced by hydrogen, and the hydrogenation is conducted at ambient temperature. The consumption of hydrogen is monitored until it reaches about two equivalents. The hydrogen is then replaced by nitrogen, and then an aqueous acid such as, for example, hydrochloric acid, is added to the autoclave. Nitrogen is replaced by hydrogen again, and hydrogenation is continued as above, while at the same time increasing the temperature of the solution to about 40°-70° C. over about 1-3 hours, when hydrogen consumption goes up by about three more equivalents. The reaction is then stopped, and the catalyst is removed by, for example, hot filtration. Cooling of the filtrates yields Tyramine hydrochloride as a solid in yields of more than 80%, with less than 2% of p-hydroxybenzoic acid contaminant. As mentioned above, the Tyramine hydrochloride may be converted to Tyramine by well known methods, if so desired.

If the above hydrogenation reaction is conducted with water present in the reaction from the beginning such as, for example, when hydrogenating 4-hydroxy ($\alpha$-chloro-$\alpha$-oximino)acetophenone in a mixture of methanol and aqueous hydrochloric acid, yields of Tyramine hydrochloride are reduced, due to the formation of p-hydroxybenzoic acid in significant amounts.

The following Examples are provided in order to further illustrate the present invention; however, the invention is no way limited thereby.

EXAMPLES

In the following Examples, g refers to grams, ml to milliliters, °C. to degrees Celsius, rpm to revolutions per minute, psi to pounds per square inch, and ambient temperature to temperatures about 21°–28° C.

EXAMPLE 1

Preparation of Tyramine hydrochloride from 4-hydroxy (α-chloro-α-oximino)acetopohenone in methanol with delayed addition of water and acid:

4-Hydroxy (α-chloro-α-oximino)acetophenone (Formula 2, 10 g, 0.05 mole) was added to a 300 ml autoclave reactor containing 10% Pd/C catalyst (2 g). The mixture was allowed to sit under hydrogen for 10 minutes, after which the reactor was degassed with nitrogen. Dry methanol (90 ml) was added via the blow case of the autoclave under nitrogen. Then the reactor was pressurized with about 50 psi of hydrogen and the reaction medium was stirred at about 1,500 rpm at ambient temperature, while monitoring pressure and hydrogen uptake. After the consumption of two equivalents of hydrogen was complete, the atmosphere in the autoclave was replaced with nitrogen, and aqueous hydrochloric acid (30 ml water containing about 2 equivalents of HCl) was added into the autoclave via its blow case. The nitrogen was again replaced by hydrogen, and the reaction continued. After consumption of another equivalent of hydrogen, external heating was started, and the internal temperature was increased from around 26° C. to about 60° C. over about 3 hours, during which two more equivalents of hydrogen were consumed. The reaction was stopped, and it was filtered hot to remove the catalyst. The filtrates, on cooling, deposited crude tyramine hydrochloride. Recrystallization from 12% HCl in water allowed isolation of crystals of Tyramine hydrochloride (80% yield) separately from p-hydroxybenzoic acid (1.3% yield).

EXAMPLE 2

Comparative Example

Preparation of Tyramine hydrochloride along with significant amounts of p-hydroxybenzoic acid:

A 300 ml autoclave was loaded with 4-Hydroxy (α-chloro-α-oximino)acetophenone (10 g, 0.05 mole), 10% Pd/C catalyst (2 g), methanol (90 ml), water (30 ml) containing one equivalent of HCl. The reactor was sealed, degassed with nitrogen, and then the nitrogen was replaced with hydrogen which was maintained at 50 psi. The reaction was stirred at 1500 rpm, and hydrogen uptake was monitored. As in Example 1, heat was applied after consumption of three equivalents of hydrogen, and the temperature was increased form about 28° C. to about 60° C. over about 4 hours. A similar work-up as in Example 1 yielded Tyramine hydrochloride in about 65% yield, the rest being p-hydroxybenzoic acid.

EXAMPLE 3

Preparation of Tyramine hydrochloride in acetic acid only:

10% Pd/C catalyst (4.4 g) containing about 50 weight percent of water was washed with glacial acetic acid (3×50 ml), and then transferred to an autoclave using fresh acetic acid (200 g). The catalyst was placed under 300 psi of hydrogen, stirred vigorously, and heated to about 45° C. over a 30 minute period. The reactor was then opened and 4-Hydroxy (α-chloro-α-oximino)acetophenone (88 g, 0.4422 m) was added, followed by acetic acid (300 g). The reaction mixture was then stirred vigorously under 300 psi of hydrogen at about 50° C. After a rapid exotherm up to about 85°–90° C., the reaction was heated to 95° C. and held there until hydrogen consumption ceased. This process took about 6 hours. The reaction was then heated to about 130° C., and the catalyst was filtered. Cooling of the filtrates gave Tyramine hydrochloride as a solid. Yields typically were in the range of 50–70%.

EXAMPLE 4

Preparation of Tyramine hydrochloride in solvent containing acid:

10% Pd/C catalyst (2.2 g) containing 50 weight percent water was washed with glacial acetic acid (3×25 ml) and then loaded into a hydrogenation reactor using fresh acetic acid (200 g). The catalyst was placed under 300 psi of hydrogen, stirred vigorously and heated to 45° C. over a 30 minute period. The reactor was then opened and 4-Hydroxy (α-chloro-α-oximino)acetophenone (88 g, 0.4422 m) was added, followed by acetic acid (240 g) that had been sparged with anhydrous HCl (4.4 g). The reaction mixture was then placed under 300 psi of hydrogen and stirred vigorously. The internal temperature was monitored and when the exothermic behavior slowed (generally around the peak temperatures of about 65°–70° C.; this reaction was generally less exothermic than the reaction in Example 3), the reaction was heated to about 95° C. When hydrogen consumption stopped, the reaction was cooled to about 25° C., and more 10% Pd/C catalyst (2.2 g) was added. The mixture was stirred and reheated to about 95° C. When hydrogen uptake ceased, water (200 g) was added. At this point, hydrogen uptake resumed and the reaction proceeded to completion. The reaction mixture was filtered to remove the catalyst, and the filtrates were evaporated to isolate Tyramine hydrochloride (yield: 80%).

What is claimed is:

1. A method of selectively producing an arylethylamine, which comprises the steps of:

(a) providing a compound of the formula:

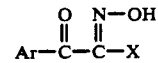

wherein X is a halide selected from F, Cl, Br, or I; and wherein Ar is an unsubstituted or substituted phenyl or naphthyl radical, wherein the substituents are selected from the group consisting of amino, alkylamino, dialkylamino, hydroxyl, alkoxy, alkyl, phenyl, benzyl, sulfonic acid, and sulfinic acid radicals, wherein the alkyl component is a branched or unbranched C1–C8 alkyl radical and wherein any of said alkyl, phenyl, and benzyl radicals are optionally substituted with one or more substituents selected from amino, hydroxyl, sulfonic acid, and sulfinic acid radicals, and said phenyl and benzyl substituents are optionally substituted with a C1–C8 alkyl or C1–C8 alkoxy radical or both;

(b) partially hydrogenating said compound of step (a) in a first hydrogenation step with hydrogen in the presence of a substantially anhydrous protic solvent and a transition metal catalyst under substantially anhydrous conditions to produce a first reaction mixture;

(c) adding water to said first reaction mixture; and (d) proceeding to further hydrogenate the reaction mixture of step (b) in a second hydrogenation step in the presence of water to produce arylethylamine salt, and (e) basifying said arylethylamine salt of step (d) to produce the arylethylamine, wherein at least one of said hydrogenation steps is carried out in the presence of an inorganic acid.

2. The method as described in claim 1, wherein said inorganic acid is present in said first hydrogenation step.

3. The method as described in claim 1, wherein said inorganic acid is present in said second hydrogenation step.

4. The method as described in claim 1, wherein said protic solvent is selected from the group consisting of alcohol, acid, ketone, ester, ether, and mixtures thereof.

5. The method as described in claim 1, wherein said protic solvent is methanol.

6. The method as described in claim 1, wherein said protic solvent is acetic acid.

7. The method as described in claim 1, wherein said inorganic acid is hydrochloric acid.

8. The method as described in claim 1, wherein said compound is present in concentrations of about 1-35 weight percent in said protic solvent in step (b).

9. The method as described in claim 1, wherein said transition metal is selected from the group consisting of platinum, palladium, nickel, rhodium, and combinations thereof.

10. The method as described in claim 1, wherein said transition metal comprises palladium.

11. The method as described in claim 1, wherein said transition metal comprises platinum.

12. The method as described in claim 1, wherein Ar is a phenyl substituted at the para position with a hydroxyl.

13. The method as described in claim 1, wherein said temperature in step (b) is about 22°-30° C.

14. The method as described in claim 1, wherein said transition metal is present in about 0.05-3 weight percent.

15. The method as described in claim 1, wherein said transition metal is present in about 0.05-1.5 weight percent.

16. The method as described in claim 1, wherein said temperature in step (d) is about 35°-120° C.

17. The method as described in claim 1, wherein said temperature in step (d) is about 35°-100° C.

18. The method as described in claim wherein said temperature in step (d) is about 40°-70° C.

19. A method of preparing Tyramine hydrochloride from 4-hydroxy (α-chloro-α-oximino)acetophenone, which comprises:

(a) providing a solution of said acetophenone in substantially anhydrous methanol in about 20 weight percent concentration;

(b) reacting said solution at temperatures of about 22°-30° C. with hydrogen in the presence of a transition metal catalyst on an inert support, in order to consume about two equivalents of hydrogen, wherein said catalyst is present in about 0.05-1.5 weight percent based on said acetophenone;

(c) adding to said reaction aqueous hydrochloric acid; and (d) continuing said reaction with hydrogen in order to consume about three more equivalents of hydrogen to produce Tyramine hydrochloride, while maintaining the temperatures at about 40°-70° C.

20. The method as described in claim 19, wherein said transition metal on inert support comprises palladium on carbon.

21. A method of preparing Tyramine hydrochloride from 4-hydroxy (α-chloro-α-oximino)acetophenone, which comprises:

(a) providing a solution of said acetophenone in a mixture of substantially anhydrous acetic acid and hydrochloric acid in about 1-35 weight percent concentration;

(b) reacting said solution at temperatures of about 20°-100° C. with hydrogen in order to consume about two equivalents of hydrogen, in the presence of a transition metal catalyst on an inert support, wherein said catalyst is present in about 0.5-5 weight percent based on said acetophenone;

(c) adding to said reaction water along with more of said catalyst; and (d) continuing said reaction with hydrogen in order to consume about three more equivalents of hydrogen, while maintaining the temperatures at about 20°-100° C., thereby forming Tyramine hydrochloride.

22. A method of preparing Tyramine hydrochloride from 4-hydroxy (α-chloro-α-oximino)acetophenone, which comprises:

(a) providing a solution of said acetophenone in a substantially an hydrous acid solvent in about 1-35 weight percent concentration, and (b) reacting said solution at temperatures of about 20°-100° C. with hydrogen in the presence of a transition metal catalyst on an inert support, in order to consume about five equivalents of hydrogen, wherein said catalyst is present in about 0.5-5 weight percent based on said acetophenone, thereby forming Tyramine hydrochloride.

23. The method as described in claim 1, wherein said transition metal catalyst in step (b) is on an inert support.

24. The method as described in claim 23, wherein said inert support is carbon.

* * * * *